(12) United States Patent
Ehwald et al.

(10) Patent No.: US 7,976,535 B2
(45) Date of Patent: Jul. 12, 2011

(54) METHOD FOR CONTROL OF THE VOLUME FLUX OF A LIQUID IN AN OSMOTIC MICROPUMP AND OSMOTIC MICROPUMP

(75) Inventors: Rudolf Ehwald, Berlin (DE); Holger Woehlecke, Berlin (DE); Helge Adleff, Berlin (DE); Max Ehwald, Berlin (DE)

(73) Assignee: Acuros GmbH, Berlin (DE)

( * ) Notice: Subject to any disclaimer, the term of this patent is extended or adjusted under 35 U.S.C. 154(b) by 605 days.

(21) Appl. No.: 11/592,922

(22) Filed: Nov. 3, 2006

(65) Prior Publication Data
US 2007/0088338 A1    Apr. 19, 2007

Related U.S. Application Data

(63) Continuation of application No. PCT/DE2005/000393, filed on Mar. 4, 2005.

(30) Foreign Application Priority Data

May 5, 2004 (DE) .......................... 10 2004 022 678

(51) Int. Cl.
*A61K 9/22* (2006.01)
(52) U.S. Cl. .................................................... 604/892.1
(58) Field of Classification Search .................. None
See application file for complete search history.

(56) References Cited

U.S. PATENT DOCUMENTS

| | | | |
|---|---|---|---|
| 4,320,758 | A | 3/1982 | Eckenhoff et al. |
| 4,619,652 | A | 10/1986 | Eckenhoff et al. |
| 2001/0047161 | A1 | 11/2001 | Wong et al. |
| 2003/0205582 | A1 | 11/2003 | Joshi et al. |

FOREIGN PATENT DOCUMENTS

| | | |
|---|---|---|
| DE | 41 06 624 A1 | 9/1992 |
| DE | 4106624 A1 * | 9/1992 |
| EP | 1167757 A3 | 1/2002 |
| WO | WO 94/05354 A | 3/1994 |

OTHER PUBLICATIONS

Theeuwes F., Yum S. I. Principles of the design and operation of generic osmotic pumps for the delivery of semisolid or liquid drug formulations. Ann. Biomed. Eng. 4 (4), 343-353 (1976), Yu-Chuan Su, Liwei Lin and Alert P.Pissano, J. of Microelectromechanical Systems 11, 736-741, 2002.
International Search Report dated Jul. 5, 2005 for corresponding International Application No. PCT/DE2005/000393.
Partial automated translation of German Patent Application No. DE 4106624 submitted in the IDS filed on Nov. 3, 2006.

* cited by examiner

*Primary Examiner* — Nicholas D Lucchesi
*Assistant Examiner* — Pritesh Patel
(74) *Attorney, Agent, or Firm* — Katten Muchin Rosenman LLP

(57) ABSTRACT

The invention refers to a method for control of a volume flow in an osmotic micropump and an osmotic micropump. According to the invention, the osmotically driven volume flow of the solvent through the sempipermeable diaphragm of an osmotic micropump is controlled by the transfer of a solute, which is not freely permeable through the diaphragm, from a source chamber to the pump's delivery chamber. According to the invention, the delivery chamber is formed as a dilution chamber, wherein the solution is flow out along a convective dilution path close to the semipermeable diaphragm. Due to the entrance of the solvent, a stationary osmotic gradient can be achieved along the convective flow path in the dilution chamber. The invention allows the maintenance and control of the flow rate. It is able to move a volume which is large in comparison to the combined volume of the source chamber and the dilution chamber.

18 Claims, 2 Drawing Sheets

US 7,976,535 B2

METHOD FOR CONTROL OF THE VOLUME FLUX OF A LIQUID IN AN OSMOTIC MICROPUMP AND OSMOTIC MICROPUMP

CROSS-REFERENCE TO RELATED APPLICATIONS

This is a continuation application of International Application No. PCT/DE2005/000393, filed Mar. 4, 2005, which claims the benefit under 35 U.S.C. 119 (a-e) of Germany Application No. 10 2004 022 678.4 filed May 5, 2004, which is herein incorporated by reference.

BACKGROUND OF THE INVENTION

1. Field of the Invention

The present invention is directed to a method for controlling the volume flow into or out of an osmotic micropump and an apparatus thereof.

2. Description of the Related Art

Micropumps are important for micro-fluidics, micro-administration of liquids and micro-injection in analytics and medical technology. Mechanical devices for driving the volume flow by electromagnetic or electrostatic forces are known, so are pumps driven by diffusion or electro-osmosis. Micropumps known as evaporation pumps and osmotic pumps are driven by diffusion. In both cases the volume flow is created by the help of a diaphragm that is permeable to the solvent.

In evaporation pumps the evaporation-caused capillary tension within the pores of the diaphragm is transduced to a flow path. They can be applied as suction pumps only and, therefore, their use in micro-fluidics is sensitive to cavitation. An example for an evaporation pump is described in EP 1167757 A3. To prevent access of non-volatile substances to the diaphragm the suction is provided by a completely evaporating liquid and a mobile separation element is applied to transduce the suction to the liquid that is to be pumped. The separation element can be, for example, a separated liquid, a movable piston, or a flexible membrane.

In electro-osmotic pumps the liquid in the pores of the semipermeable diaphragm is moved by an electric current through the diaphragm, the driving force being created at the electric double layers within the pores. This requires fixed charges in the pores of the applied diaphragm. Electro-osmotic pumps can be used in micro-fluidics for distinct purposes. Their advantage over evaporation or osmotic pumps consists in good controllability of the flow rate. Their disadvantages are low energy efficiency, high waste heat and inability to create a high pressure difference.

In osmotic pumps the volume flow is caused by diffusion of the permeable solvent within the semipermeable diaphragm or within a diffusion layer at its surface.

Osmotic pumps have the advantage of high energy efficiency. By their help a difference in chemical potential can be transformed into volume work without strong heat development. They can be applied without electrical power supply for generation of suction and pressure and they are able to overcome high back pressure. They can be used for delivery of liquids, as has been described for example in US 2001/0047161 and U.S. Pat. No. 4,320,758. In these pumps a solvent, e.g. water, permeates through a semipermeable diaphragm into a chamber that is filled with the solution of non-permeable solvent and wherein the pressure can be increased due to the osmotically driven volume flow. This chamber may be built either as a closed working chamber with expandable volume that is covered by a flexible membrane, or as an open delivery chamber, from which the solution is driven through an outlet. Osmotic micro-pumps are commercially available and can be used, e.g., for delivery of drugs into the interstitium or veins.

The liquid leaving the delivery chamber of an osmotic pump contains the osmotically effective solute. This is not a disadvantage as a matter of principle, since it is possible to bring a movable separation element between this liquid and the liquid to be administrated, as described e.g. in DE 4106624 A1. The entrance of the solvent into the solution within the expandable working chamber or within the open delivery chamber causes progressive solute dilution and, in consequence, a progressive decrement of the flow rate. A high volume and/or a mixing device in the working or delivery chamber would be required to minimize this decrement. However, the dilution effect can be prevented by filling the working chamber with salt crystals or other soluble solid material, which is dissolved at solvent entrance and generates a saturated solution of the solute in equilibrium with its solution (Theeuwes F., Yum S. I. Principles of the design and operation of generic osmotic pumps for the delivery of semi-solid or liquid drug formulations. Ann. Biomed. Eng. 4 (4), 343-354 (1976), Yu-Chuan Su, Liwei Lin and Alert P. Pissano, J. of Microelectromechanical Systems 11, 736-741, 2002). Osmotic pumps using a solution equilibrium in this way are able to deliver a volume flow with constant velocity against high back pressure. Nevertheless, the volume delivered with constant rate remains limited. It is given by the ratio between the mass of the solid solute in the chamber and the concentration of its saturated solution. In the case of sodium chloride it is not much larger than the volume of the delivery chamber. The delivered liquid contains the solute at its saturation concentration, although a much lower concentration is sufficient for creating enough pressure for most applications. The limited ratio between the volume of the saturated solution that can be delivered and the volume of the pump is a technical shortcoming with respect to miniaturisation.

The task for the present invention consists in the provision of a method and a device for controlling a volume flux driven by an osmotic micropump with a delivery chamber, which is not limited by the volume of the delivery chamber.

SUMMARY OF THE INVENTION

Therein, the present invention is a method for controlling the volume flow into or out of an osmotic micropump consisting in transfer of an osmotically effective solute from a source chamber into a dilution chamber that is bordered by a semipermeable diaphragm and forms a path for convective flow, wherein a solution is driven along the diaphragm by the entrance of the solvent and wherein this flow is restricted spatially to the reach of solute diffusion close to the surface of the diaphragm.

The method according to this invention consists in the transfer of an osmotically effective solute from an external source chamber into the delivery chamber or a part of the delivery chamber of an osmotic pump. The delivery chamber is built as a dilution chamber, since it forms a convective path for the solution from the site of solute entrance to the outlet and since the flow is restricted spatially to the reach of solute diffusion close to the surface of the diaphragm. The solution is diluted by the entrance of the solvent. Due to the spatial restriction of the flow path to a zone close to the semi-permeable diaphragm the concentration gradient created by solvent entrance extends along the membrane and therefore can reach a stationary state in short time, if the solute introduction is carried out at a constant rate. The solute may be introduced into the dilution chamber by diffusion or iontophoresis through pores or by convective flow using an auxiliary pump. The velocity of the stationary flow delivered by the pump depends on the rate by which the solute is moved from the source chamber into the dilution chamber.

The osmotic micropump according to the invention comprises a delivery chamber for the out-flowing solution that is built as a dilution chamber. The dilution chamber is bordered by a semipermeable diaphragm. This diaphragm separates the lumen of the dilution chamber containing the solution from the permeable solvent. The lumen of the dilution chamber represents a path for convective flow that is extended along the semipermeable diaphragm from the site of solute input to the outlet. Introduction of a solute into the dilution chamber in combination with the osmotic flow of the solvent into this chamber results in a stationary volume flow along the semipermeable diaphragm and brings about a stationary state of dilution with a stationary concentration gradient of the solute along the length of the flow path.

According to the invention, the dilution chamber is connected with a source chamber that is storing a solute which is not freely permeable through the diaphragm of the dilution chamber. This solute may be a pure liquid substance or it may be dissolved to form a concentrated solution. It may be useful to store the solute in the source chamber as a dispersion of the non-dissolved solid substance in its saturated solution. The osmotic micropump according to this invention can be applied as a suction pump for the liquid solvent or as a solution delivering pump or both.

In a variant of the invention at least one source chamber is connected hydraulically by pores with the delivery chamber. The pores are permeable for the solute, which can enter the dilution chamber by diffusion. Although the diffusion of the solute through the pores into the delivery chamber is generally coupled to counter-diffusion of the solvent, this must not decrease the concentration gradient in the pores before the stored amount of the solute within the source chamber is strongly depleted. There are several means to prevent dilution of the solute in the source chamber. One possibility consists in filling the source chamber with the dispersion of non-dissolved solute in its saturated solution. A further possibility consists in filling the source chamber with a solute that exists as pure liquid, e.g. polyethylene glycol, to use water as the solvent and to add a water absorbing material, e.g. water-free sodium sulfate crystals to the source chamber. Binding of water to the crystals keeps the organic solution free of water. Since the source chamber is not expandable, the introduction of the organic solute or the salt using the possibilities described above does not contribute to the volume flow but controls the osmotic volume flow.

Iontophoresis is another way for solute transfer according to the invention. The dilution chamber, which is in contact with water through the semipermeable diaphragm, can be combined with two source chambers through pores, while the source chambers are filled with the aqueous dispersion of salt crystals in saturated salt solution. If the source chambers are supplied with electrodes, anions and cations may be driven by iontophoresis into the dilution chamber, thus controlling the osmotic volume flow into and out of the pump.

In a further variant of the invention the source chamber is connected with the dilution chamber by an auxiliary pump delivering an auxiliary flow of concentrated solution into the dilution path. The auxiliary pumping device itself may be a conventional osmotic micropump with a delivery chamber containing the solute as dispersion of non-dissolved particles in their saturated solution. In the latter case, it is useful to have an auxiliary osmotic micropump that absorbs the solvent from the diluted solution released by the dilution chamber at the end of the dilution path. The diluted solution delivered by the dilution chamber may be conducted along the diaphragm of the auxiliary osmotic pump without suction and hence, without the danger of cavitation.

Generally, it can be useful to supply the osmotic micropump according to the invention with a diaphragm that consists of porous hydrophobic material and is not permeable to liquid water and aqueous solutions but is permeable to water vapour. Suitable diaphragms of this kind are available in the form of flat or capillary membranes consisting of porous polytetrafluoroethylene or polypropylene. These diaphragms show an ideal semipermeability to water and non-volatile solutes. Such membranes may be applied as semipermeable diaphragms either at the auxiliary pump or at the dilution chamber or both. The mechanism of osmosis through such diaphragms is isothermal distillation. The strong temperature dependence of this process can be used to control the flow rate over a wide range of rates. The defined and low permeability of the above mentioned membranes for water is favourable for the control of small flow rates. The osmotic micropump according to the invention differs from known osmotic pumps by the method of flow control. This method consists in introduction of solute into a delivery chamber that is formed as a dilution chamber as described above. The volume flow out of the dilution chamber can be kept at a constant rate for a long time. The flow rate can also be modulated by increasing or decreasing the rate by which the solute is introduced to the convective dilution path within the dilution chamber. Flow control in the osmotic pump constructed according to the invention is comparable to osmo-regulation of volume flow in physiological systems, e.g. phloem transport in plants, but in contrast to osmotic pumps acting in physiological systems, control of the osmotic steady state is based on artificial and controllable devices.

For the construction of the micropump according to this invention it may be useful to build the semipermeable diaphragm as a capillary membrane. In this case, the reservoir for the solvent, e.g. water, can be placed outside of the capillary membrane and the dilution chamber can be formed by the capillary lumen, or vice versa. Alternatively, the semipermeable diaphragm may be a flat membrane that separates a dilution path from the solvent reservoir.

In this case, the convective dilution path can be built by one or more channels or a flat transfusable particle bed that is bordered by the membrane.

The dilution chamber according to this invention can be used as a pump that delivers a volume flow or to take up a liquid volume from a matrix, e.g. the interstitium of the subcutaneous tissue. The liquid to be taken up can be the pure solvent, e.g. water or a solution of permeable solutes. The latter case is interesting for sampling low-molecular-weight solutes from a liquid-saturated matrix. For this application, the dilution chamber may be an ultrafilter or microfilter membrane that is permeable for the substance to be sampled, further, the solute stored in the source chamber is impermeable due to the large size of its colloids but hydraulically effective. Suitable solutes for this purpose are high-molecular-weight polyethylene glycol or polystyrolsulfonate. If the capillary ultrafilter membrane representing the dilution chamber is lead through the liquid matrix, a small auxiliary flow of the polymer solution causes the transfer of the ultrafiltrate out of the matrix to the outlet of the pump.

BRIEF DESCRIPTION OF THE DRAWING

The invention is elucidated by examples of realisation, as described in FIGS. 1-4.

DETAILED DESCRIPTION OF THE INVENTION

Figure 1:
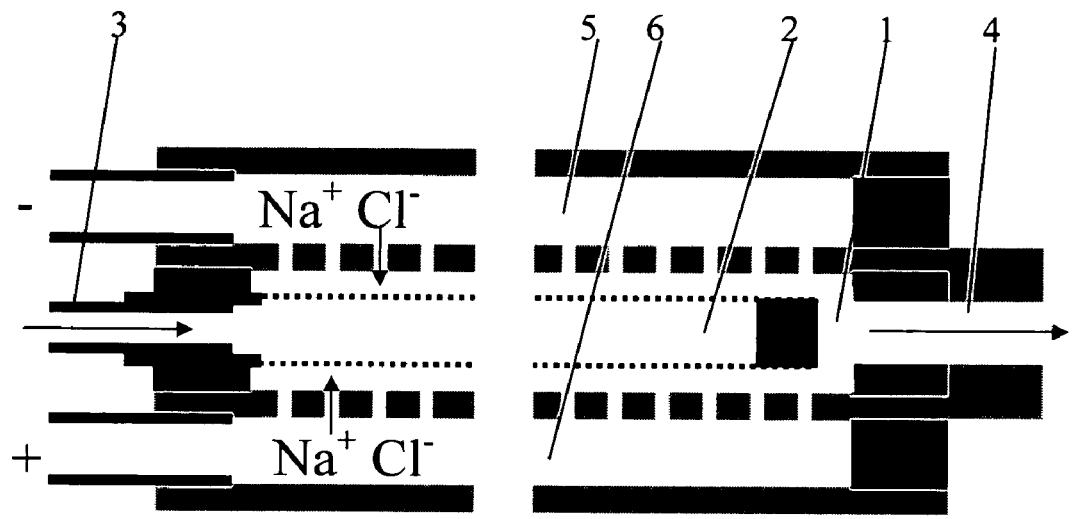
FIG. 1 shows the scheme of an osmotic micropump, wherein the solute is a salt and the volume flow is controlled by iontophoresis of its ions from two source chambers into the dilution chamber.

FIG. 1 demonstrates a variant of the invention, wherein the transfer of the solute, a salt, is controlled by iontophoresis. In the central channel 1 there is a semipermeable capillary membrane 2 consisting of porous polypropylene, which is permeable for water vapour and impermeable to ions. This capillary membrane forms a hollow fibre that is closed at one end. It is connected at the other end to a capillary 3 for delivery of the solvent, in this case water. The space between the capillary membrane and the channel walls is open to the outlet 4. This space acts as a dilution chamber. The wall of the central channel 1 contains pores, which connect this channel to channels 5 and 6 which are filled with saturated salt solution and which are connected to a current source. Channels 5 and 6 act as source chambers. In the absence of electric current the flow rate is controlled by net salt diffusion through the pores into the dilution chamber. Application of an electric current through the pores results in additional net salt transport into the dilution chamber by iontophoresis through the pores. This variant of the invention enables direct control of the osmotic pump by an electric current.

Figure 2:
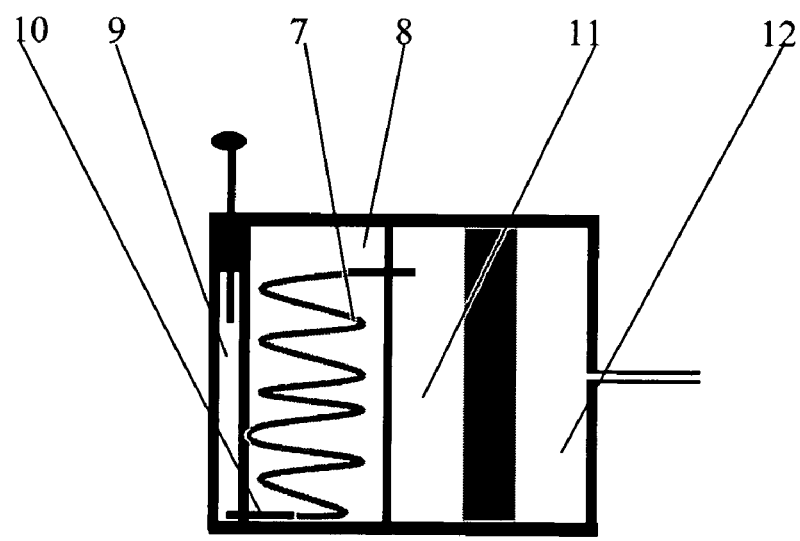
FIG. 2 shows the scheme of an osmotic micropump, wherein the volume flow can be controlled by an auxiliary flow of concentrated solution or liquid solute from a source chamber to the dilution chamber using an auxiliary mechanical pump.

FIG. 2 shows a variant of the osmotic micropump according to the invention, wherein the osmotic flow is controlled by an auxiliary mechanic pump. The dilution chamber of this pump is represented by the lumen of a hollow fibre segment 7 with an inner diameter of ca. 300 μm. The wall of the hollow fibre 7 is a dialysis membrane consisting of regenerated cellulose that is highly permeable to water and impermeable to PEG 2000, a polyethylene glycol with a molecular weight of 2000 g/Mol. The hollow fibre is situated within a water reservoir 8. Its lumen, about 30 μl, is connected at one end to the source chamber 9 of a mechanical pump by means of a capillary 10. At the other end the lumen of the hollow fibre is connected to the space behind the piston of a syringe 11. The source chamber 9 of the mechanical pump is filled with a solution of PEG 2000 with a concentration of 500 g per liter. The space between the outlet of the syringe and the piston 12 is filled with the liquid to be administered. Transfer of only 1 μl of the solution into the dilution chamber results in a long-standing osmotic flow of the liquid out of the pump, which exceeds 20 μl. If the mechanical pump delivers small volume pulses, the flow rate can be controlled by the frequency of these pulses.

Figure 3:
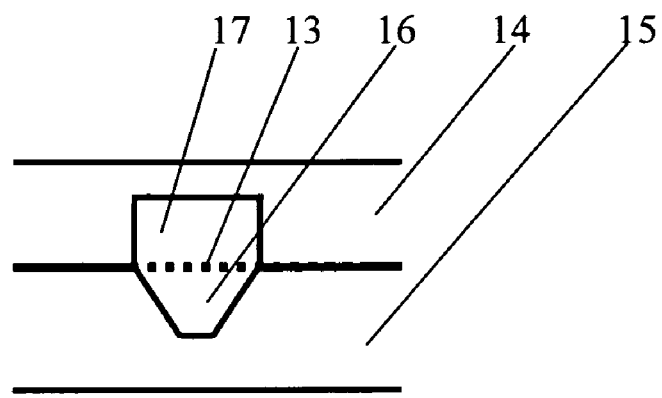
FIG. 3 shows the scheme of an osmotic micropump applicable for suction of solutions containing permeable solutes through a flat diaphragm.

FIG. 3 shows a cross section through the semipermeable diaphragm and the dilution chamber of an osmotic suction pump according to the invention. The pump is controlled by an auxiliary flow of an osmotically effective polymer solution. The semipermeable diaphragm 13 is a flat microfilter membrane with a pore size of ca. 50 nm. It separates the two channels 16 and 17 within the solid plates 14 and 15. The lower channel 16 in the solid plate 15 is a blind ending one. It contains a solution of electrolytes and proteins (Stokes' diameter less than 10 nm) which can permeate through the diaphragm into the upper channel 17. Channel 17 represents the dilution chamber. The non-permeable solute used in this osmotic micropump is sodium polystyrolsulfonate with a molar mass of 2.000 kDa and a Stokes' diameter larger than 50 nm. The concentration of this polymer is 50 mg/ml. A controlling auxiliary micro-flow of the polystyrolsulfonate solution is delivered to one end of the channel 17 by a mechanical syringe pump. In this case, the solvent water together with the permeable solutes, including proteins, is moved osmotically from channel 16 to channel 17. Through the outlet at the end of channel 17, a solution of all solutes, including polystyrolsulfonate, leaves the pump, whereas the solution of the permeable protein is sucked into channel 17. The flow rate in both channels is controlled by the auxiliary flow of the polystyrolsulfonate solution into channel 17. In contrast to an evaporation pump the described osmotic micropump can move a solution through the diaphragm without accumulation of their solutes before the membrane.

Figure 4:
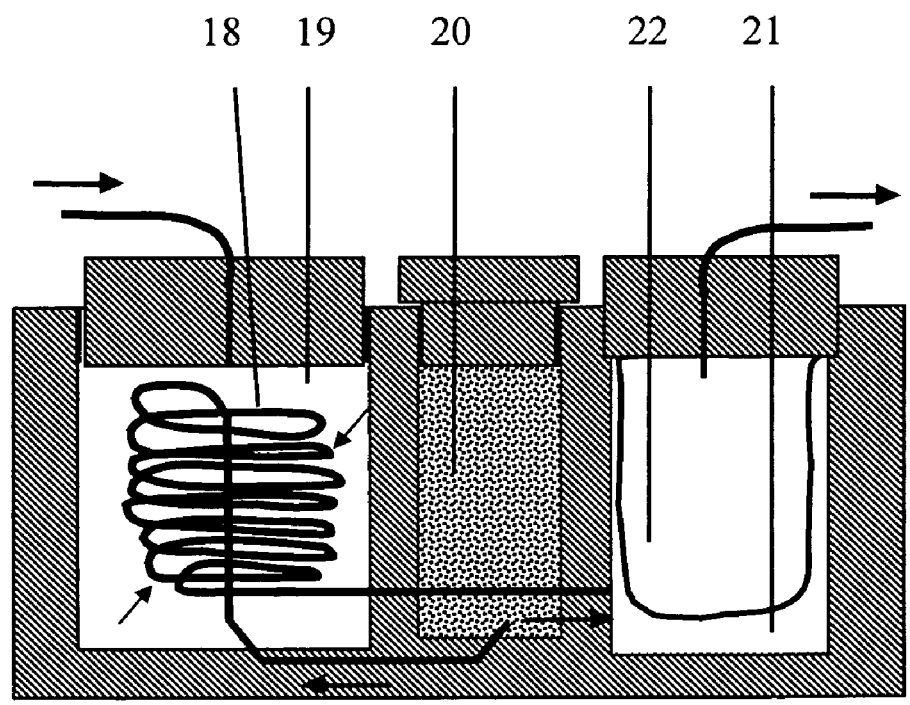
FIG. 4 shows the scheme of an osmotic micropump with an osmotic auxiliary pump, wherein solvent is taken up into the delivery chamber of the auxiliary pump from the diluted solution leaving the dilution chamber.

FIG. 4 shows an osmotic micropump according to the invention that uses a conventional osmotic pump as auxiliary pump. The delivery chamber of this auxiliary pump builds the source chamber 20. The dilution chamber is built by a porous hydrophobic capillary membrane 18 (Membrana GmbH, Wuppertal, Germany). This capillary membrane forms a flexible hollow fibre, the inner diameter of which is 300 μm, while its length is 120 cm. The capillary membrane is permeable to water vapour and impermeable to non-volatile components of the liquid phase. The capillary membrane is situated within a water-filled chamber 19. At one end it is connected to the lumen of the source chamber 20. The source chamber is completely filled with a dispersion of sodium chloride crystals in saturated sodium chloride solution. The other end of the capillary membrane 18 is led through the source chamber into a third chamber. Here, a flexible membrane consisting of latex rubber separates the diluted salt solution 21 leaving the dilution chamber from the liquid 22 to be administered by the pump. At constant temperature this pump provides a volume flow with constant rate, as long as the salt solution within the source chamber is saturated. Water is taken up osmotically by the saturated salt solution in the source chamber 20 from the diluted salt solution flowing within the short hollow fibre segment through the source chamber. This solvent flux drives saturated solution into the dilution chamber represented by the long hollow fibre segment 18. Here it is diluted by water entering from the water-filled chamber 19. In contrast to conventional osmotic pumps based on salt dissolution equilibrium, the volume delivered by this pump can exceed the combined volume of the salt chamber and dilution chamber by at least one order of magnitude.

The invention claimed is:

1. A method of controlling the volume flow into or out of an osmotic micropump, the osmotic micropump comprising:
    a source for an osmotically active solute in a form of a liquid substance, a dispersion of non-dissolved particles in a saturated solution, or a concentrated solution;
    a supply of a solvent;
    a lumen comprising a self-sustaining convective flow of solute from the source chamber to an exit, the lumen comprising a semi-permeable membrane;

the method comprising steps of:
(a) absorbing an amount of concentrated solute from the source chamber into a first portion of the lumen;
(b) absorbing a solvent for driving a solution of the solute along a second portion of the lumen by lowering a concentration of the solute in the solution;
(c) increasing the concentration of the solute in a third portion of the lumen to maintain the flow; and
(d) using iontophoresis or convection for controlling the transfer of the osmotically effective solute from the source into the lumen.

2. An osmotic micropump comprising:
a source chamber, a solvent chamber, and an exit; each chamber separated from the other chambers;
the source chamber storing an osmotically active solute in a form of a liquid substance, a dispersion of non-dissolved particles in a saturated solution, or a concentrated solution;
the solvent chamber comprising a supply of a solvent;
a lumen comprising a self-sustaining convective flow of solute from the source chamber to the exit, the lumen comprising a semi-permeable membrane, the lumen comprising
a first portion connected to the source chamber for taking an amount of concentrated solute into the lumen;
a second portion disposed in the solvent chamber, the second portion receiving the solute from the first portion, the second portion absorbing the solvent to drive a solution of the solute along the lumen by lowering a concentration of the solute in the solution;
a third portion disposed in the source chamber for increasing the concentration of the solute in the solution to maintain the flow, and
a fourth portion connected with the exit to exit the solution of the solute.

3. Osmotic micropump according to claim 2, further comprising a means for electro-migration of the solute.

4. Osmotic micropump according to claim 2, wherein increasing the concentration of the solute in the solution in the third portion acts as an auxiliary pump.

5. Osmotic micropump according to claim 2, wherein the lumen comprises the solute as a dispersion of a non-dissolved substance in its saturated solution.

6. Osmotic micropump according to claim 5, wherein the lumen comprises a closed end in the first portion.

7. Osmotic micropump according to claim 2, wherein the semi-permeable membrane comprises a flat or capillary membrane, the semi-permeable membrane comprising a hydrophobic porous material that is permeable to water vapour but non-permeable to liquid water.

8. The osmotic micropump according to claim 2, wherein the micropump is used in the field of micro-fluidics, micro-analytics, administration and sampling of liquids.

9. An osmotic micropump comprising:
a source chamber, a solvent chamber and an exit;
the source chamber storing an osmotically active solute in a form of a liquid substance, a dispersion of non-dissolved particles in a saturated solution, or a concentrated solution;
the solvent chamber comprising a supply of a solvent;
a lumen comprising a sustainable convective flow of solute from the source chamber to an exit, the lumen comprising a semi-permeable membrane, the lumen comprising
a first portion in fluid communication with the source chamber for taking an amount of solute into the lumen;
a second portion receiving the solute from the first portion, the second portion absorbing the solvent to drive a solution of the solute along the lumen by lowering a concentration of the solute in the solution.

10. The osmotic micropump of claim 9, further comprising a means for electro-migration of the solute from the source chamber to the lumen.

11. The osmotic micropump of claim 9, wherein the source chamber further comprises a semi-permeable membrane for absorbing solvent into the source chamber to sustain the flow.

12. The osmotic micropump of claim 11, wherein the semi-permeable membrane comprised by the source chamber is in fluid communication with the second portion of the lumen.

13. The osmotic micropump of claim 9, wherein the lumen comprises a third portion disposed in the source chamber for increasing the concentration of the solute in the solution to sustain the flow.

14. The osmotic micropump of claim 13, wherein the lumen comprises a forth portion connected with the exit to exit the solution of the solute.

15. The osmotic micropump of claim 9, wherein the semi-permeable membrane is a hollow fiber.

16. The osmotic micropump of claim 13, wherein the third portion is a hollow fiber.

17. The osmotic micropump of claim 9, wherein the lumen acts as a dilution chamber.

18. The osmotic micropump of claim 9, further comprising a micro-fluidic device.

\* \* \* \* \*